United States Patent
Yamagata et al.

(10) Patent No.: US 9,253,414 B2
(45) Date of Patent: Feb. 2, 2016

(54) IMAGING-OBSERVATION APPARATUS

(71) Applicant: Panasonic Corporation, Osaka (JP)

(72) Inventors: Michihiro Yamagata, Osaka (JP);
Norihiro Imamura, Osaka (JP);
Tsuguhiro Korenaga, Osaka (JP);
Takashi Okada, Osaka (JP); Yoshimitsu Noguchi, Gifu (JP)

(73) Assignee: Panasonic Intellectual Property Management Co., Ltd., Osaka (JP)

( * ) Notice: Subject to any disclaimer, the term of this patent is extended or adjusted under 35 U.S.C. 154(b) by 403 days.

(21) Appl. No.: 13/947,727

(22) Filed: Jul. 22, 2013

(65) Prior Publication Data
US 2014/0028825 A1    Jan. 30, 2014

(30) Foreign Application Priority Data

Jul. 25, 2012 (JP) ................................. 2012-164708

(51) Int. Cl.
*H04N 5/262* (2006.01)
*A61B 5/00* (2006.01)

(52) U.S. Cl.
CPC ............ *H04N 5/2621* (2013.01); *A61B 5/0077* (2013.01); *A61B 5/444* (2013.01); *A61B 5/7425* (2013.01)

(58) Field of Classification Search
USPC ..................................................... 348/77, 46
See application file for complete search history.

(56) References Cited

U.S. PATENT DOCUMENTS

| 2011/0288385 | A1* | 11/2011 | Stamatas | A61B 5/4875 600/306 |
| 2013/0038690 | A1* | 2/2013 | Mitchell | A61B 1/00193 348/46 |

FOREIGN PATENT DOCUMENTS

| JP | 2010-088599 A | 4/2010 |
| JP | 2011-097987 A | 5/2011 |
| JP | 2012-024140 A | 2/2012 |

* cited by examiner

*Primary Examiner* — Nigar Chowdhury
(74) *Attorney, Agent, or Firm* — Renner, Otto, Boisselle & Sklar, LLP

(57) ABSTRACT

An imaging-observation apparatus according to the present disclosure includes: an image capturing section that shoots a subject under multiple different shooting optical conditions at the same time and sequentially generates a plurality of images under those multiple different shooting optical conditions; a display control section that accepts an operator's input; an image synthesizing section that synthesizes together the plurality of images in accordance with the input to the display control section at a synthesis ratio specified by the input and sequentially generates synthetic images one after another; and a display section that presents the synthetic images.

18 Claims, 15 Drawing Sheets

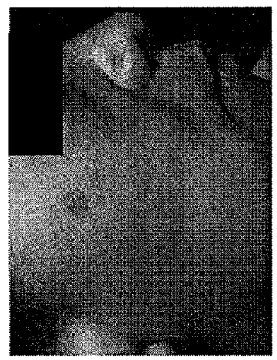 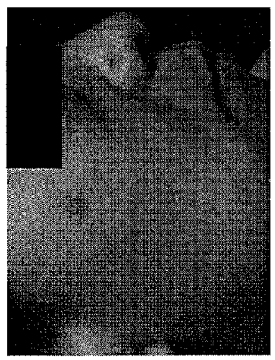 
 
FIG.2

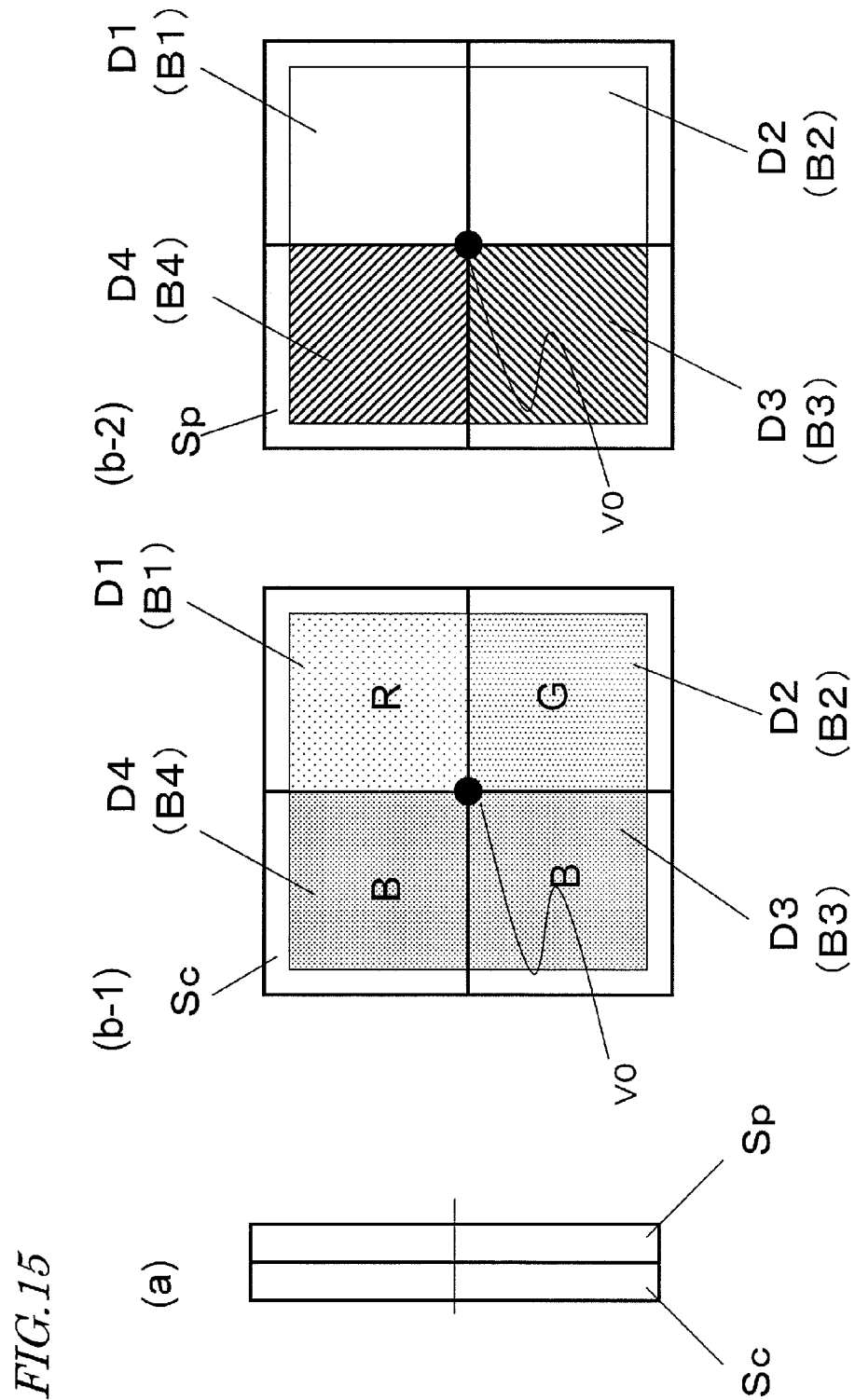

IMAGING-OBSERVATION APPARATUS

BACKGROUND

1. Technical Field

The present disclosure relates to an imaging-observation apparatus which shoots an image of a portion of an organism such as its surface and neighboring region and which displays such an image shot.

2. Description of the Related Art

Recently, as more and more people have been paying increasing attention to how to improve or maintain their beautiful appearance, there have been growing demands for instruments or devices for beauty treatments. Among other things, when some person tries to sell a cosmetic product or beauty treatment device to someone else, it has become even more important to observe and analyze the latter person's skin state on the spot.

Observation of skin state includes observing the skin surface texture or wrinkles and observing the subcutaneous tissue at spots, for example. To observe the subcutaneous tissue accurately, skin surface information and subcutaneous tissue information are suitably obtained separately. It is known that in order to get such observation done, the skin surface may be irradiated with predetermined polarized light and shot through a polarizer. Then, an image, of which the majority is surface reflected light components with surface information, and an image, of which the majority is internally reflected light components with subcutaneous tissue information, can be shot separately.

For example, Japanese Laid-Open Patent Publication No. 2010-88599 (which will be referred to herein as "Patent Document No. 1" for convenience sake) discloses a camera which includes a polarized light source for observing the skin surface and another polarized light source for observing subcutaneous tissue in order to change the modes of observation from observing the texture by monitoring the light reflected from the skin surface into observing spots or dullness by monitoring the light reflected from under the skin surface, and vice versa. This camera sequentially shoots a skin surface observed image, a subcutaneous tissue observed image, and a natural light image by turning ON those light sources sequentially and by turning them ON simultaneously.

Meanwhile, in the field of medical treatments, by irradiating an organism with illuminating light and by imaging the light that has been reflected from the organism, information about any change in the color at the surface of the organism or its structural change is obtained, thereby diagnosing his or her diseased region. In making such a diagnosis, shooting sessions are often carried out with not only natural light but also polarized light as well in order to diagnose the disease more easily.

For instance, Japanese Laid-Open Patent Publication No. 2012-24140 (which will be referred to herein as "Patent Document No. 2" for convenience sake) discloses a system which sequentially irradiates a subject with multiple polarized light beams with mutually different polarization states and sequentially images reflected parts of those polarized light beams one after another, thereby monitoring the status of the diseased region. In this system, a polarization property image with a predetermined polarization property is generated based on a plurality of images that have been shot, and some portion of that polarization property image which is specified by reference to the information on a parameter table that has been prepared in advance is highlighted by pseudo color display, for example.

And Japanese Laid-Open Patent Publication No. 2011-97987 (which will be referred to herein as "Patent Document No. 3" for convenience sake) discloses a method for generating an image in which the components of the light that has been reflected from the internal tissue are enhanced by adding or subtracting the pixel values of multiple images that have been shot with the polarized light conditions changed and synthesizing together the images that have been shot under different polarized light sources.

SUMMARY

According to the conventional methods described above, however, two or more images that have been produced by light beams with mutually different polarization states are displayed, and therefore, sometimes it is difficult to find a spot or diseased region on the images. Thus, a non-limiting exemplary embodiment of the present application provides an imaging-observation apparatus that can display an easily observable image by increasing the visibility of the subject in the vicinity of the surface of the targeted organism.

An imaging-observation apparatus according to an aspect of the present disclosure includes: an image capturing section configured to shoot a subject under multiple different shooting optical conditions at the same time and sequentially generate a plurality of images under those multiple different shooting optical conditions; a display control section configured to accept an operator's input; an image synthesizing section configured to synthesize together the plurality of images in accordance with the input to the display control section at a synthesis ratio specified by the input and to sequentially generate synthetic images one after another; and a display section which is configured to present the synthetic images.

An imaging-observation apparatus according to another aspect of the present disclosure includes: an image capturing section configured to shoot a subject under multiple different shooting optical conditions at the same time and generate a plurality of images under those multiple different shooting optical conditions; a display control section configured to accept an operator's input; an image synthesizing section configured to synthesize together the plurality of images to generate a synthetic image, the image synthesizing section generating a first synthetic image by synthesizing together the plurality of images in accordance with a first input that has been entered through the display control section at a synthesis ratio specified by the first input, and generating a second synthetic image by synthesizing together the plurality of images in accordance with a second input that has been entered after the first input through the display control section at a synthesis ratio specified by the second input; and a display section configured to present the first synthetic image and then the second synthetic image.

An imaging-observation apparatus according to still another aspect of the present disclosure includes: an image capturing section configured to shoot a subject under multiple different shooting optical conditions at the same time and generate a plurality of images under those multiple different shooting optical conditions; a display control section configured to accept an operator's input; an image synthesizing section configured to synthesize together the plurality of images to generate a synthetic image, the image synthesizing section generating a first synthetic image by synthesizing together a first plurality of images that have been generated by the image capturing section at a first time in accordance with a first input that has been entered through the display control section at a synthesis ratio specified by the first input, and generating a second synthetic image by synthesizing together a second plurality of images that have been generated by the image capturing section at a second time after the first time in accordance with a second input that has been entered after the first input through the display control section at a synthesis ratio specified by the second input; and a display section configured to present the first synthetic image and then the second synthetic image.

An imaging-observation apparatus according to an aspect of the present disclosure can synthesize together transitional moving pictures, which fall between a plurality of images that have been shot under mutually different shooting optical conditions such as polarization directions, in real time in accordance with the operator's instruction and can display the synthetic image as a moving picture. As a result, an imaging-observation apparatus which allows the user to sense more easily any difference that has been caused between image shots due to a difference in shooting condition is realized.

This general and particular aspect can be implemented as a system, a method, a computer program or a combination thereof.

Other benefits and advantages of an embodiment disclosed herein will become apparent from the following description and attached drawings. Those benefits and/or advantages can be provided individually by various embodiments and the matter that is disclosed in the description and drawings. It should be noted, however, that not everything needs to be provided to achieve one or two or more similar ones of those benefits and advantages.

BRIEF DESCRIPTION OF THE DRAWINGS

FIG. 2 shows examples of images shot by the two image capturing sections of the first embodiment and also shows examples of synthetic images generated.

FIGS. 15($a$), 15($b$-1) and 15($b$-2) illustrate another exemplary configuration for an area-divided color filter and an area-divided polarizer according to the third embodiment.

DETAILED DESCRIPTION

Figure 1:
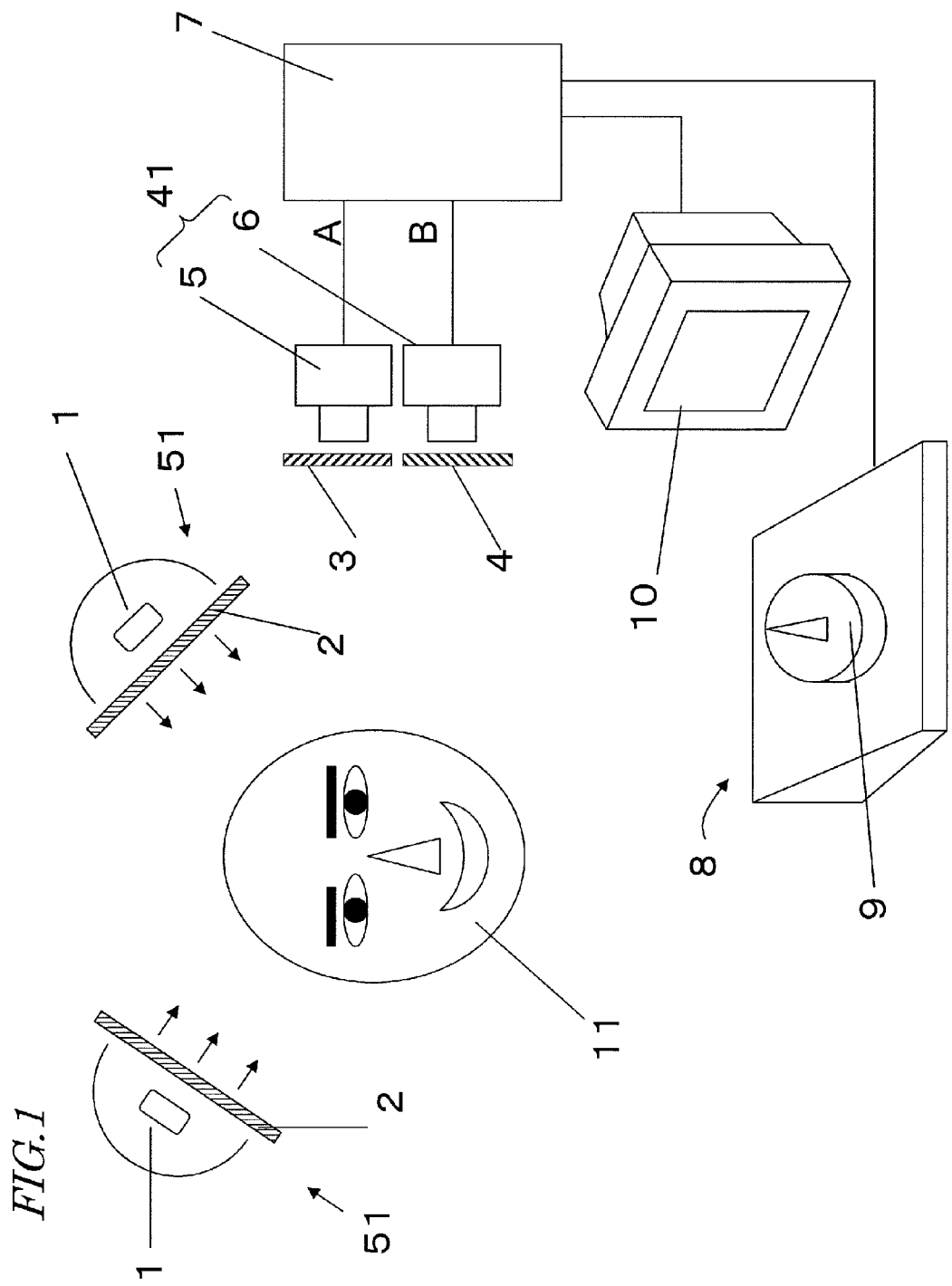
FIG. 1 illustrates a general configuration for a first embodiment of an imaging-observation apparatus according to the present disclosure.

In observing a spot on a person's skin or monitoring a diseased portion of an organism, sometimes such a spot or diseased portion needs to be located easily or observable in real time.

According to the method for shooting a natural light image by providing two polarized light sources as disclosed in Patent Document No. 1, after a natural light image which should be a familiar one to the observer daily has been presented to him or her, a skin surface observed image and a subcutaneous tissue observed image are presented. However, this method is not designed to compare any difference between those images, and it is not always easy to detect spots according to such a method.

On the other hand, according to the method disclosed in Patent Document No. 2 in which a parameter table is provided for a polarization property image and some portion of the table is highlighted, a lot more computations need to be done, and therefore, such a method is not suitable for making a simple measurement in real time. Likewise, the method disclosed in Patent Document No. 3 is not suitable for making a simple measurement in real time, either.

Thus, to overcome these problems with the related art, the present inventors invented a novel imaging-observation apparatus.

An imaging-observation apparatus according to an aspect of the present disclosure includes: an image capturing section configured to shoot a subject under multiple different shooting optical conditions at the same time and sequentially generate a plurality of images under those multiple different shooting optical conditions; a display control section configured to accept an operator's input; an image synthesizing section configured to synthesize together the plurality of images in accordance with the input to the display control section at a synthesis ratio specified by the input and to sequentially generate synthetic images one after another; and a display section configured to present the synthetic images. By adopting such a configuration, any difference between images that have been shot under multiple different shooting conditions can be checked out as a moving picture in response to the operator's operation, and therefore, such a difference can be viewed more easily.

The shooting optical conditions may include at least one of the polarization direction and wavelength of light to generate the plurality of images. If the polarization directions and wavelengths of light are different as shooting optical conditions, pieces of internal information can be collected separately from multiple different depths under the surface of an organism and observed images specific to those wavelengths can be obtained. As a result, an observed image can be obtained according to the intended purpose.

The imaging-observation apparatus may further include a polarized light source that emits mostly polarized light with a predetermined polarization direction, and the subject may be irradiated with the polarized light. According to such an embodiment, in shooting a person's skin or an organism, surface reflected light components and light components that have been scattered inside the tissue and then reflected can be observed separately.

The multiple different shooting optical conditions may include a condition for shooting an image of the subject by getting the polarized light transmitted through a polarizer, of which the polarization axis is parallel to the predetermined polarization direction, and/or a condition for shooting an image of the subject by getting the polarized light transmitted through a polarizer, of which the polarization axis is perpendicular to the predetermined polarization direction. If the polarizer has a polarization axis that is parallel to the polarization direction, surface reflected components can be observed mostly, and therefore, the skin texture and pores can be observed effectively when this apparatus is used to observe a person's skin. On the other hand, if the polarizer has a polarization axis that is perpendicular to the polarization direction, spots under the skin can be observed effectively.

The multiple different shooting optical conditions may include a first condition for shooting an image of the subject by getting the polarized light transmitted through a polarizer, of which the polarization axis is parallel to the predetermined polarization direction, and a second condition for shooting an image of the subject by getting the polarized light transmitted through a polarizer, of which the polarization axis is perpendicular to the predetermined polarization direction. By adopting both of these two shooting conditions, both the skin texture and pores and the spots can be observed at the same time.

The multiple different shooting optical conditions may include a shooting condition for shooting an image of the subject by getting the polarized light transmitted through no polarizer at all. According to such an embodiment, an image shot of the skin which looks as natural as when the skin is seen with the naked eye can be obtained. In addition, since that image and a polarized image shot can be compared and checked out as a moving picture in response to the operator's operation, it can be seen how the spot image that has been shot under the polarized light shooting condition would look when seen with the naked eye.

The multiple different shooting optical conditions may include a condition for shooting the subject with light beams falling within multiple different wavelength ranges. According to such an embodiment, even if a part of the organism's tissue causes a phenomenon such as absorption of light or emission of phosphorescence in a predetermined wavelength range, the difference between the targeted tissue and its surrounding tissue can be seen easily and effectively.

The multiple different wavelength ranges may include at least one of an ultraviolet range and an infrared range. According to such an embodiment, shooting can be carried out in wavelength ranges other than the visible radiation range. For example, as an infrared beam penetrates deeper into an organism, the blood flow under the surface of the tissue can be observed. Meanwhile, as an ultraviolet beam gets absorbed into a subcutaneous spot easily, the spot can be observed more easily.

The image capturing section may include a plurality of image capture devices with respectively independent optical systems. According to such an embodiment, images can be shot under multiple different optical conditions at the same time.

The imaging-observation apparatus may further include a first polarizer, the plurality of image capture devices may include a first image capture device, and the first polarizer may be arranged between the subject and the first image capture device. According to such an embodiment, an image produced by light with a predetermined polarization direction can be selectively shot based on the light reflected from the subject.

The first polarizer may have a polarization axis which is either parallel or perpendicular to the predetermined polarization direction. According to such an embodiment, when a person's skin or an organism is shot, components of light reflected from the surface and components of light that has been scattered inside of a tissue and then reflected can be observed separately.

The imaging-observation apparatus may further include a second polarizer, the plurality of image capture devices may include a second image capture device, the second polarizer may be arranged between the subject and the second image capture device, and the first and second polarizers may have mutually different polarization axis directions. According to such an embodiment, images can be shot simultaneously under multiple different polarization conditions.

The polarization axis of the first polarizer may be parallel to the predetermined polarization direction and the polarization axis of the second polarizer may be perpendicular to the predetermined polarization direction. According to such an embodiment, an image produced by polarized light, of which the axis of polarization is perpendicular to the polarization direction of a polarized light source, and an image produced by polarized light, of which the axis of polarization is parallel to the polarization direction of the polarized light source, can be both obtained. Specifically, when this apparatus is used to observe a person's skin, not only an image representing his or her skin's spot more effectively but also an image representing his or her skin's texture more effectively can be obtained.

The plurality of image capture devices may consist of the first and second image capture devices alone. According to such a configuration, the overall cost of the apparatus can be cut down with a person's skin texture and spot observed at the same time. In addition, according to such a configuration, an image that would be seen with the naked eye can be obtained by synthesizing those two images shot together.

The plurality of image capture devices may include at least one image capture device with no polarizer arranged between the subject and itself. According to such an embodiment, an image that would be seen with the naked eye can be shot directly.

The image capturing section may include a plurality of image capture devices, at least one of which may have a different shooting wavelength range from the other image capture devices'. According to such an embodiment, even if a part of the organism's tissue causes a phenomenon such as absorption of light or emission of phosphorescence in a predetermined wavelength range, the difference between the targeted tissue and its surrounding tissue can be seen easily and effectively.

The at least one image capture device's shooting wavelength range may be one of the infrared and ultraviolet wavelength ranges, and the shooting wavelength range of the other image capture devices may be the other of the infrared and ultraviolet wavelength ranges. According to such an embodiment, shooting can be carried out in wavelength ranges other than the visible radiation range. For example, as an infrared beam penetrates deeper into an organism, the blood flow under the surface of the tissue can be observed. Meanwhile, as an ultraviolet beam gets absorbed into a subcutaneous spot easily, the spot can be observed more easily.

The image capturing section may include: a stop; an image capturing optical system; an image sensor with multiple groups of pixels, each group of pixels being made up of a plurality of pixels; an area-divided optical element which is arranged in the vicinity of the stop and which has at least two optical regions, through which light beams are transmitted with mutually different optical properties; and an array of optical elements which is arranged between the image capturing optical system and the image sensor and which makes the light beams that have been transmitted through the predetermined optical regions of the area-divided optical element incident on mutually different groups of pixels of the image sensor. The image capturing section may be configured to generate multiple images from the multiple groups of pixels. According to such a configuration, the image capturing section may be configured to have only one optical system, and therefore, the overall size of the apparatus can be reduced.

The area-divided optical element may have an optical property that makes light beams transmitted through the at least two optical regions have mutually different polarization directions. According to such an embodiment, a plurality of images can be shot under multiple different polarization conditions using a single image capturing section.

In the area-divided optical element, the polarization direction of a light beam transmitted through one of the at least two optical regions may be parallel to the predetermined polarization direction. According to such an embodiment, an image produced by the light that has been transmitted through that optical region can be used effectively to observe a person's skin texture or pores as pieces of his or her skin surface information.

In the area-divided optical element, the polarization direction of a light beam transmitted through one of the at least two optical regions may be perpendicular to the predetermined polarization direction. According to such an embodiment, the light that has been scattered right under the skin and reflected can be imaged, and therefore, a spot under the skin can be observed effectively.

In the area-divided optical element, the polarization direction of a light beam transmitted through one of the at least two optical regions may be parallel to the predetermined polarization direction and the polarization direction of a light beam transmitted through the other of the at least two optical regions may be perpendicular to the predetermined polarization direction. According to such an embodiment, a person's skin texture and spots can be observed at the same time using a single image capture device.

The number of the at least two optical regions may be two. According to such an embodiment, in a configuration that can observe both a person's skin texture and spots at a time using a single image capturing section, the aperture can be broadened under each shooting condition, and a decrease in sensitivity can be minimized.

The area-divided optical element may further include an optical region that transmits a light beam that is not polarized in any direction. According to such an embodiment, an image that looks as natural as what is seen with the naked eye can be obtained.

In the area-divided optical element, the at least two optical regions may have mutually different spectral transmittances. By adopting such a configuration, a plurality of images produced by light beams falling within multiple different wavelength ranges can be shot at the same time with a single image capturing section.

In the area-divided optical element, one of the at least two optical regions may be configured to selectively transmit either an ultraviolet beam or an infrared beam. According to such an embodiment, a single image capturing section can carry out shooting both with an infrared beam and with an ultraviolet beam.

The plurality of images may be moving pictures, the synthetic image may be a synthetic moving picture, and the display section may be configured to display the synthetic moving picture. According to such an embodiment, the apparatus can monitor the subject in real time, and will come in handier.

An imaging-observation apparatus according to another aspect of the present disclosure includes: an image capturing section configured to shoot a subject under multiple different shooting optical conditions at the same time and generate a plurality of images under those multiple different shooting optical conditions; a display control section configured to accept an operator's input; an image synthesizing section configured to synthesize together the plurality of images to generate a synthetic image, the image synthesizing section generating a first synthetic image by synthesizing together the plurality of images in accordance with a first input that has been entered through the display control section at a synthesis ratio specified by the first input, and generating a second synthetic image by synthesizing together the plurality of images in accordance with a second input that has been entered after the first input through the display control section at a synthesis ratio specified by the second input; and a display section configured to present the first synthetic image and then the second synthetic image.

An imaging-observation apparatus according to still another aspect of the present disclosure includes: an image capturing section configured to shoot a subject under multiple different shooting optical conditions at the same time and generate a plurality of images under those multiple different shooting optical conditions; a display control section configured to accept an operator's input; an image synthesizing section configured to synthesize together the plurality of images to generate a synthetic image, the image synthesizing section generating a first synthetic image by synthesizing together a first plurality of images that have been generated by the image capturing section at a first time in accordance with a first input that has been entered through the display control section at a synthesis ratio specified by the first input, and generating a second synthetic image by synthesizing together a second plurality of images that have been generated by the image capturing section at a second time after the first time in accordance with a second input that has been entered after the first input through the display control section at a synthesis ratio specified by the second input; and a display section configured to present the first synthetic image and then the second synthetic image.

Hereinafter, embodiments of an imaging-observation apparatus according to the present disclosure will be described with reference to the accompanying drawings. In the following description of embodiments, the imaging-observation apparatus is supposed to shoot a person's face skin as a subject and observe it.

Embodiment 1

FIG. 1 is a schematic representation illustrating a first embodiment of an imaging-observation apparatus according to the present disclosure. The imaging-observation apparatus of this embodiment includes polarized light sources 51, polarizers 3, 4, an image capturing section 41, an image synthesizing section 7, a display control section 8, and a display section 10.

Each of the polarized light sources 51 includes a light source 1 and a polarizer 2. The light source 1 may emit a white light beam, for example. The polarizer 2 has an axis of polarization which is parallel to a predetermined direction and is arranged so as to transmit the light that has been emitted from the light source 1. As a result, the polarized light source 51 emits a white polarized light beam which is polarized in the predetermined direction. In this embodiment, the imaging-observation apparatus includes two polarized light sources 51 in order to irradiate the subject 11 more uniformly with polarized light beams. In this embodiment, the subject 11 is a person's face. However, if no shadow is cast on a portion of the subject 11 to be observed (e.g., when the surface of the subject 11 has little unevenness or when the subject 11 is a small one), only one polarized light source 51 may be used. Still alternatively, the imaging-observation apparatus may include three or more polarized light sources 51 as well. If the apparatus includes a plurality of polarized light sources 51, then those polarized light sources 51 may be arranged so that the polarized light beams emitted from them have the same polarization direction.

Each of the polarizers 3 and 4 has an axis of polarization. The polarizer 3 is arranged so that its axis of polarization is parallel to the predetermined direction. On the other hand, the polarizer 4 is arranged so that its axis of polarization is perpendicular to the predetermined direction. That is to say, the respective axes of polarization of these polarizers 3 and 4 have mutually different directions. The respective axes of polarization of the polarizers 2 and 3 are parallel to each other, and the respective axes of polarization of the polarizers 2 and 4 are perpendicular to each other. In this description, if two axes of polarization are "parallel to each other", then it means herein that the two axes of polarization form an angle of approximately 180±15 degrees, more suitably, approximately 180±10 degrees. On the other hand, if two axes of polarization are "perpendicular to each other", then it means herein that the two axes of polarization form an angle of approximately 90±15 degrees, more suitably, approximately 10 degrees. This is because even if the difference of the angle formed by those two axes from 180 degrees or 90 degrees is within ±15 degrees, the polarized light with substantially sufficient intensity can be transmitted or cut off. And if the difference from 180 degrees or 90 degrees is within ±10 degrees, the polarized light can be transmitted or cut off even more effectively.

The image capturing section 41 includes a plurality of image capture devices (cameras) with respectively independent optical systems. In this embodiment, the image capturing section 41 includes two image capture devices 5 and 6. Also, in this embodiment, each of the image capture devices 5 and 6 can shoot a moving picture and a still picture. And the image capture devices 5 and 6 output either moving pictures or still pictures as images A and B, respectively. These images A and B may be either color images or monochrome images.

The image capturing section 41 includes the image capture devices 5 and 6, and therefore, can generate a plurality of moving pictures or still pictures sequentially by shooting the subject 11 at the same time. In addition, since the axes of polarization of the polarizers 3 and 4 have mutually different directions, the shooting optical conditions of the image capture devices 5 and 6 are different from each other, too. That is to say, in this embodiment, the "shooting optical condition" is the polarization direction of polarized light. Also, in this description, if the subject 11 is shot "at the same time", it means herein that the subject 11 is shot with the light that has come from the subject at the same point in time. Nevertheless, images obtained by shooting do not always have to be generated at the same time.

The image synthesizing section 7 receives signals representing the images A and B from the image capturing section 41, synthesizes the images A and B at the synthesis ratio specified by the input to the display control section 8 in accordance with the input, and sequentially generates synthetic images one after another. The image synthesizing section 7 may be implemented as a signal processor to generate an image or an information processor such as a microcomputer. If there is parallax between the images A and B, the image synthesizing section 7 performs pattern matching between the images using one of the two images A and B as a reference image, thereby determining the magnitude of parallax. And after having shifted the other image based on the magnitude of parallax thus obtained, the image synthesizing section 7 synthesizes together the shifted image and the reference image.

The display section 10 may be a display such as an LCD and displays the synthetic image that has been generated by the image synthesizing section 7.

The display control section 8 accepts an operator's input in response to his or her operation and outputs the information thus entered to the image synthesizing section 7. In this embodiment, the display control section 8 includes a control dial 9, and as the operator turns the dial 9, a different kind of signal is output according to the angle of rotation. The subject 11 may naturally be the operator's face skin but may also be another person's face skin. With the imaging-observation apparatus of this embodiment, even when the operator is observing his or her face skin by him- or herself, he or she can find or locate a spot on his or her face easily, because this apparatus is very easy to operate for him or her.

Next, it will be described how this imaging-observation apparatus operates. The light that has been emitted from the light source 1 of each polarized light source 51 is transmitted through the polarizer 2 to be a polarized light beam, which is polarized in a predetermined direction and which irradiates the subject 11. Then, the light reflected from the subject 11 is transmitted through the polarizers 3 and 4 and incident on the image capture devices 5 and 6, respectively.

Generally speaking, if a person's skin is irradiated with light, the reflected light includes light that has been reflected from his or her skin surface and light that has been reflected from inside of his or her skin. If the emitted light is polarized light which is polarized in a particular direction, then the light reflected from the surface includes a lot of polarization components that are parallel to the light illuminating the subject, because the polarization components of the illuminating light are maintained in such a situation. On the other hand, the light reflected from inside of the skin includes both polarization components that are parallel to the illuminating light and polarization components that are perpendicular to the illuminating light, because the light is affected by scattering inside of the skin and its polarization state is not maintained. That is why if a person's skin is irradiated with polarized light and if the reflected light is imaged via a polarizer through which polarized light that is parallel to the polarization direction of the illuminating light is transmitted, then an image including more information about the skin surface than an ordinary image shot can be obtained. Such an image can be used effectively to observe the skin texture, for example. On the other hand, if the reflected light is imaged via a polarizer which transmits polarized light that is perpendicular to the illuminating light, then an image including more information about the subcutaneous tissue than an ordinary image shot can be obtained. Such an image can be used effectively to observe skin spots, for example.

In this embodiment, the image A shot by the image capture device 5 includes more information about the skin surface, while the image B shot by the image capture device 6 includes more information about the subcutaneous tissue. FIG. 2 shows examples of images shot. Specifically, the images 21 and 22 are the images A and B that have been shot by the image capture devices 5 and 6, respectively. The image 21 includes a lot of components of the light reflected from the skin surface and represents, in an enhanced form, the shininess and shadows caused by reflection. On the other hand, the image 22 includes a lot of components of the light scattered under the skin, and has had its shiny portions removed from the skin.

To observe spots, an image including a lot of information about the internal tissue (such as the image 22) may be monitored to find locations which have a different color from the surrounding. Nevertheless, just by reference to such an image including a lot of information about the internal tissue (e.g., the image 22) alone, sometimes it may be difficult to determine whether the difference in color is caused by the light reflected from under the skin or by the shadows involved with the skin surface texture. The decision may be made by comparing an image including a lot of surface information (such as the image 21) to the image including a lot of internal tissue information (such as the image 22). However, the image including a lot of surface information (such as the image 21) and the image including a lot of internal tissue information (such as the image 22) have significantly different brightness values due to a difference in the quantity of light reflected. That is why those two images will give the viewer so different overall impressions that it is difficult for him or her to sense their subtle differences.

Thus, according to this embodiment, the operator gets synthetic images C presented on the display section 10 one after another with the synthesis ratio of the images A and B changed by turning the control dial 9 on the display control section. The synthetic images 23 to 25 shown in FIG. 2 are obtained by synthesizing together those images 21 and 22 at predetermined ratios. Specifically, the synthetic image 23 is obtained by synthesizing the images 21 and 22 together at a ratio of one to three. The synthesis ratios of the other images 24 and 25 are one to one and three to one, respectively. In this manner, by generating synthetic images while changing the synthesis ratios of the images A and B that have been captured by the image capture devices 5 and 6, a moving picture changing between the images A and B can be generated.

Figure 3:
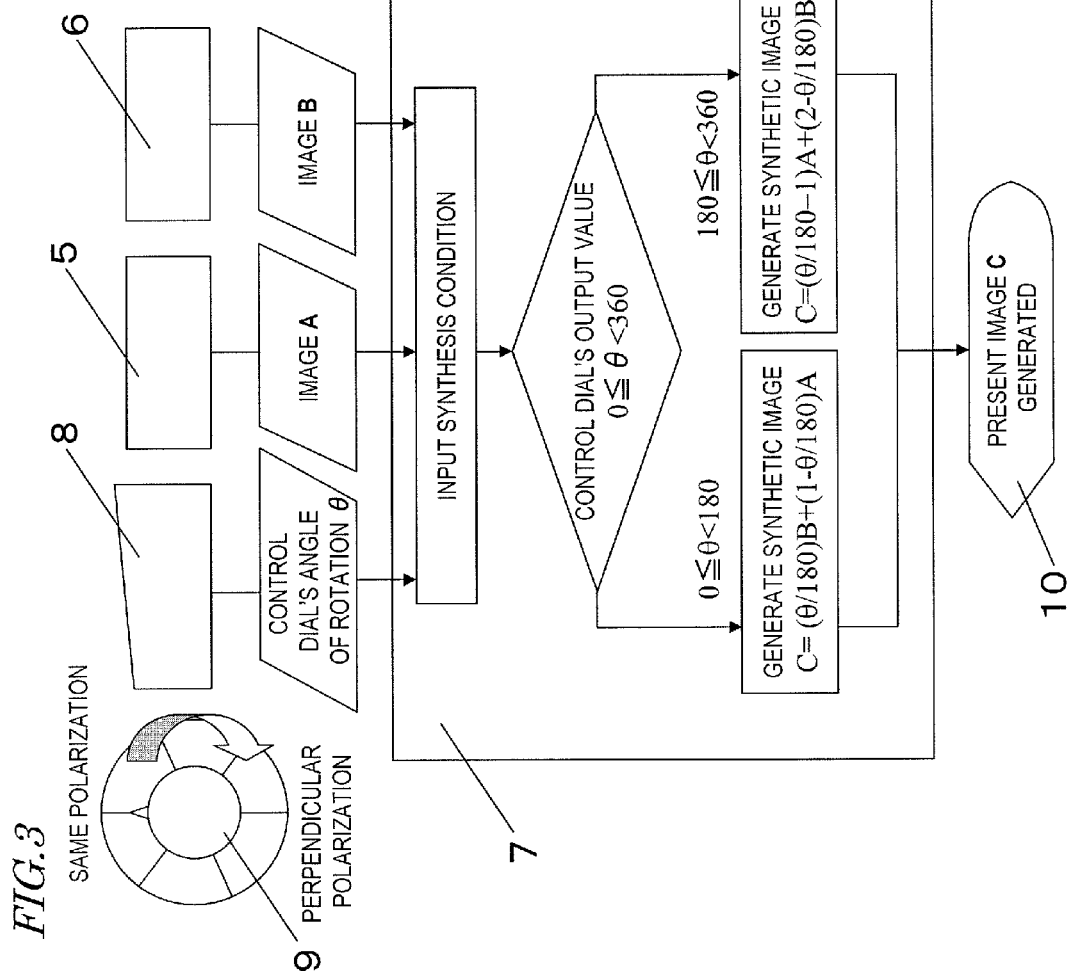
FIG. 3 is a flowchart showing a general procedure of the image synthesis processing to be carried out by the image synthesizing section of the first embodiment.

FIG. 3 is a flowchart showing a general procedure of the image synthesis processing to be carried out by the image synthesizing section 7. The image synthesizing section 7 receives not only signals representing the images A and B from the image capture devices 5 and 6 but also information representing the angle of rotation θ of the control dial 9 of the display control section 8.

The control dial 9 can be turned within an angular range of 0 through 360 degrees with respect to a reference direction, which may be the twelve o'clock direction in the example illustrated in FIG. 3 if the control dial 9 is compared to the face of an analog clock. Specifically, if the angle of rotation is 0 degrees, the image A which is produced by the reflected light that is parallel to the polarization direction of the polarized light source 51 is displayed. On the other hand, if the angle of rotation is 180 degrees, the image B which is produced by the reflected light that is polarized perpendicularly to the polarization direction of the polarized light source 51 is displayed.

The image synthesizing section 7 synthesizes together the images A and B by the following Equations (1) according to the range in which the angle θ falls, thereby generating synthetic images C one after another. Those synthetic images C generated will be sequentially presented on the moving picture display 10:

$$C = \frac{\theta}{180} \cdot B + \left(1 - \frac{\theta}{180}\right) \cdot A \quad (1)$$
$$(0 \leq \theta < 180)$$
$$C = \left(\frac{\theta}{180} - 1\right) \cdot A + \left(2 - \frac{\theta}{180}\right) \cdot B$$
$$(180 \leq \theta < 360)$$

The image synthesizing section 7 may carry out this series of image synthesis processing steps over and over again every time the θ value changes. Alternatively, the image synthesizing section 7 may perform this series of image synthesis processing steps at regular time intervals (e.g., every predetermined number of frames), no matter how much θ changes. As a result, as the operator turns the control dial 9 halfway through from 0 degrees to 180 degrees, the moving picture display 10 presents, as a moving picture 31, how the image A changes gradually into the image B, i.e., how the image 21 including a lot of surface information changes into the image 22 including a lot of internal tissue information, according to the angle of the control dial 9. Consequently, the operator can observe such a series of images of the subject 11 as a moving picture continuously. On the other hand, if the operator turns the dial from over 180 degrees through 360 degrees, then a moving picture, in which the image changes from the image B into the image A in reverse direction to the one indicated by the arrow on the moving picture 31, will be presented. In that case, the images A and B do not have to be still pictures but may also be generated sequentially by the image capture devices 5 and 6 as the time passes. In other words, the images A and B themselves may change sequentially while the control dial 9 is turned. In that case, the images on the display can be changed from an image including a lot of surface information (such as the image 21) into an image including a lot of internal tissue information (such as the image 22) with the subject 11 shot in real time.

As can be seen, the image presented on the display section 10 changes from the image A into the image B, or vice versa, as the control dial 9 is turned. As a result, the operator can observe a series of changing images as a moving picture and can locate the spots more easily thanks to increased visibility. On the other hand, if the operator is shooting him- or herself as the subject 11, his or her own images change with his or her operation. Consequently, he or she can readily change his or her images to present instantaneously according to his or her intention (e.g., may get the same set of changing images presented a number of times back and forth or may stop presenting the moving picture at a timing when the synthesis ratio reaches a one that requires careful observation), and therefore, can see more easily how his or her images change.

That is why this embodiment can be used effectively to observe a person's skin using a polarized light source. In particular, spots that could not be seen easily under an ordinary illuminance source can be checked out effectively.

Embodiment 2

Figure 4:
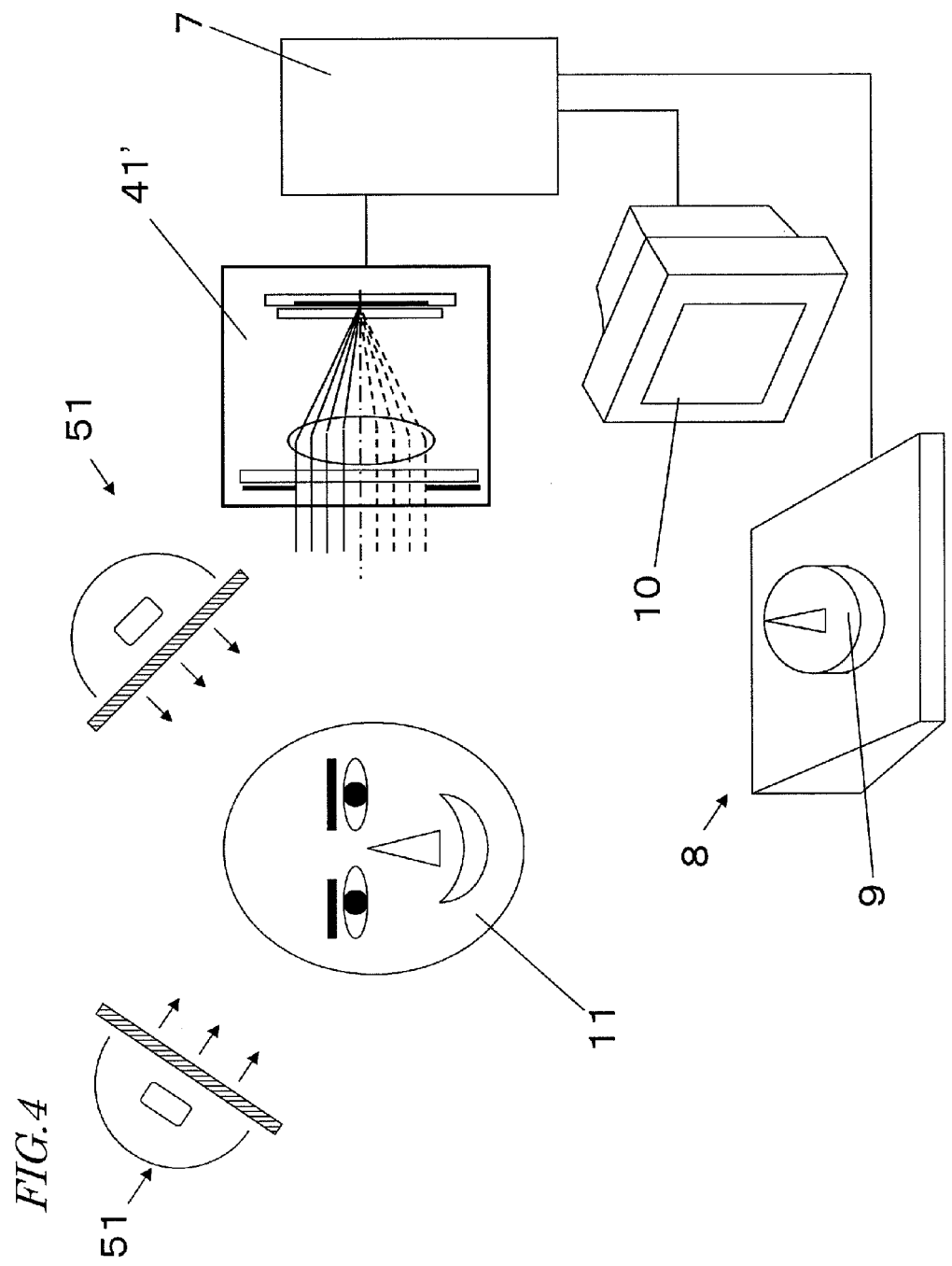
FIG. 4 illustrates a general configuration for a second embodiment of an imaging-observation apparatus according to the present disclosure.

FIG. 4 is a schematic representation illustrating a second embodiment of an imaging-observation apparatus according to the present disclosure. The imaging-observation apparatus of this embodiment includes an image capturing section 41' instead of the image capturing section 41, which is a major difference from the first embodiment. Thus, the following description of this embodiment will be focused on the structure of the image capturing section 41'.

Figure 5:
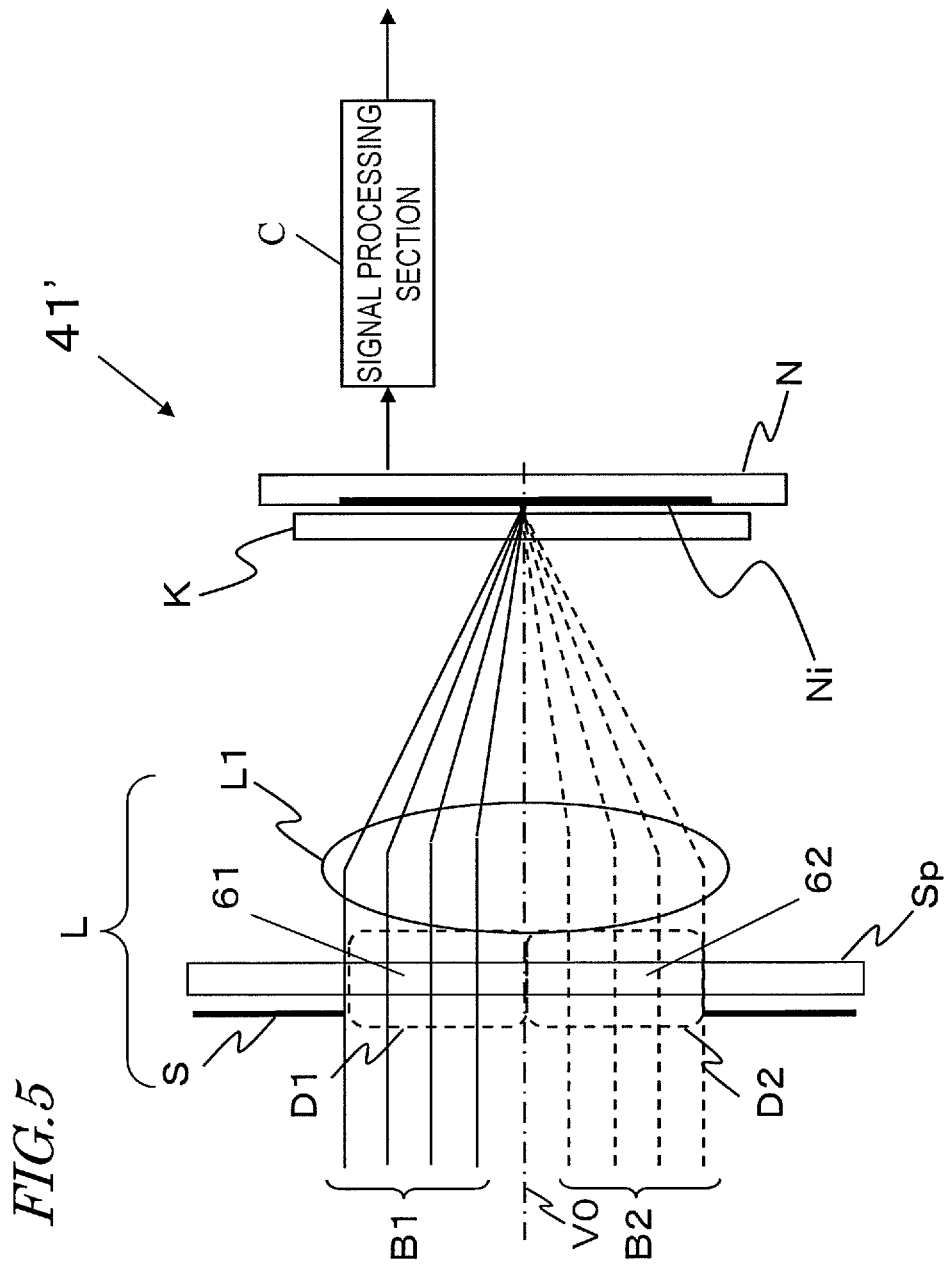
FIG. 5 illustrates a configuration for an image capturing section according to the second embodiment.

FIG. 5 schematically illustrates the structure of the image capturing section 41', which can get images produced by polarized light beams with multiple different polarization directions using a single image capture device.

As shown in FIG. 5, the image capturing section 41' includes a lens optical system L of which the optical axis is identified by V0, an array of optical elements K which is arranged in the vicinity of the focal point of the lens optical system L, and an image sensor N.

The lens optical system L includes a stop S and an objective lens L1 which images the light that has been transmitted through the stop S onto an image sensor. On a plane that intersects with the optical axis V0 at right angles, the lens optical system L is divided by a line that passes through the optical axis V0 and includes two optical regions D1 and D2 which run parallel to each other along the optical axis V0. An area-divided polarizer Sp is arranged in the vicinity of the stop S.

Figure 6:
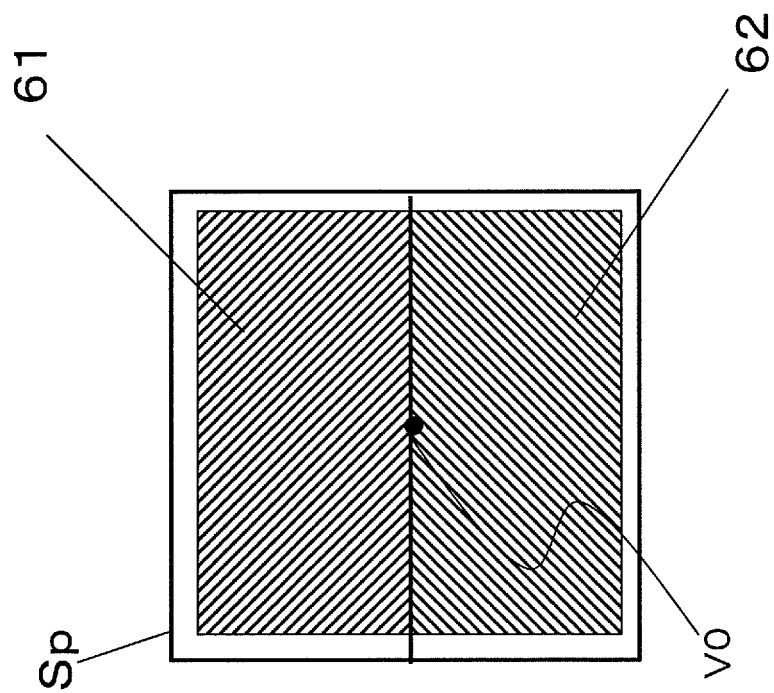
FIG. 6 illustrates a configuration for an area-divided polarizer according to the second embodiment.

FIG. 6 is a front view of the area-divided polarizer Sp. On a plane that intersects with the optical axis V0 at right angles, the area-divided polarizer Sp includes two areas 61 and 62 which are divided by a line that passes through the optical axis V0. In the area 61, arranged is a polarizer which transmits a polarized light beam that is parallel to the polarization direction of the polarized light source 51. On the other hand, in the area 62, arranged is a polarizer which transmits a polarized light beam that is perpendicular to the polarization direction of the polarized light source 51.

As shown in FIG. 5, the area-divided polarizer Sp is arranged in the lens optical system L so that the areas 61 and 62 of the area-divided polarizer Sp are located in the optical regions D1 and D2, respectively. Two bundles of rays B1 and B2 are transmitted through the optical regions D1 and D2, respectively. In this case, by being transmitted through the areas 61 and 62 of the area-divided polarizer Sp, the bundle rays B1 turns into a polarized light beam which is polarized parallel to the polarization direction of the polarized light source 51, and the bundle of rays B2 turns into a polarized light beam which is polarized perpendicularly to the polarization direction of the polarized light source 51. These bundles of rays B1 and B2 are further transmitted through the objective lens L1 and the array of optical elements K in this order to reach the image capturing plane Ni of the image sensor N as shown in FIG.

Figure 7:
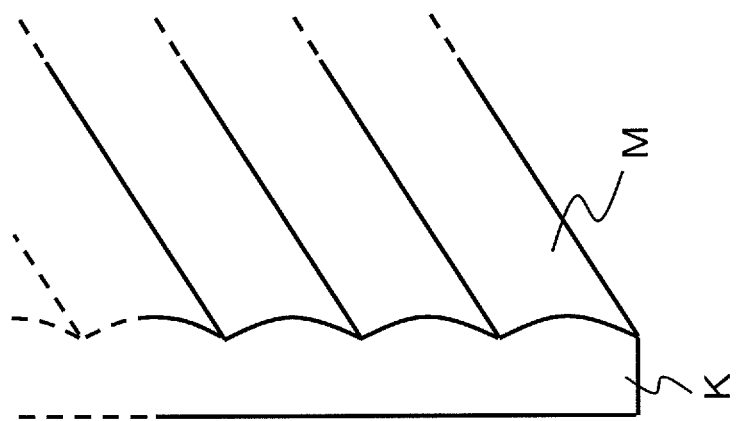
FIG. 7 is a perspective view illustrating an array of optical elements according to the second embodiment.

FIG. 7 is a perspective view of the array of optical elements K shown in FIG. 5. The array of optical elements K is a lenticular lens in which cylindrical optical faces M are arranged periodically on the light-outgoing side of the lens.

Figure 8:
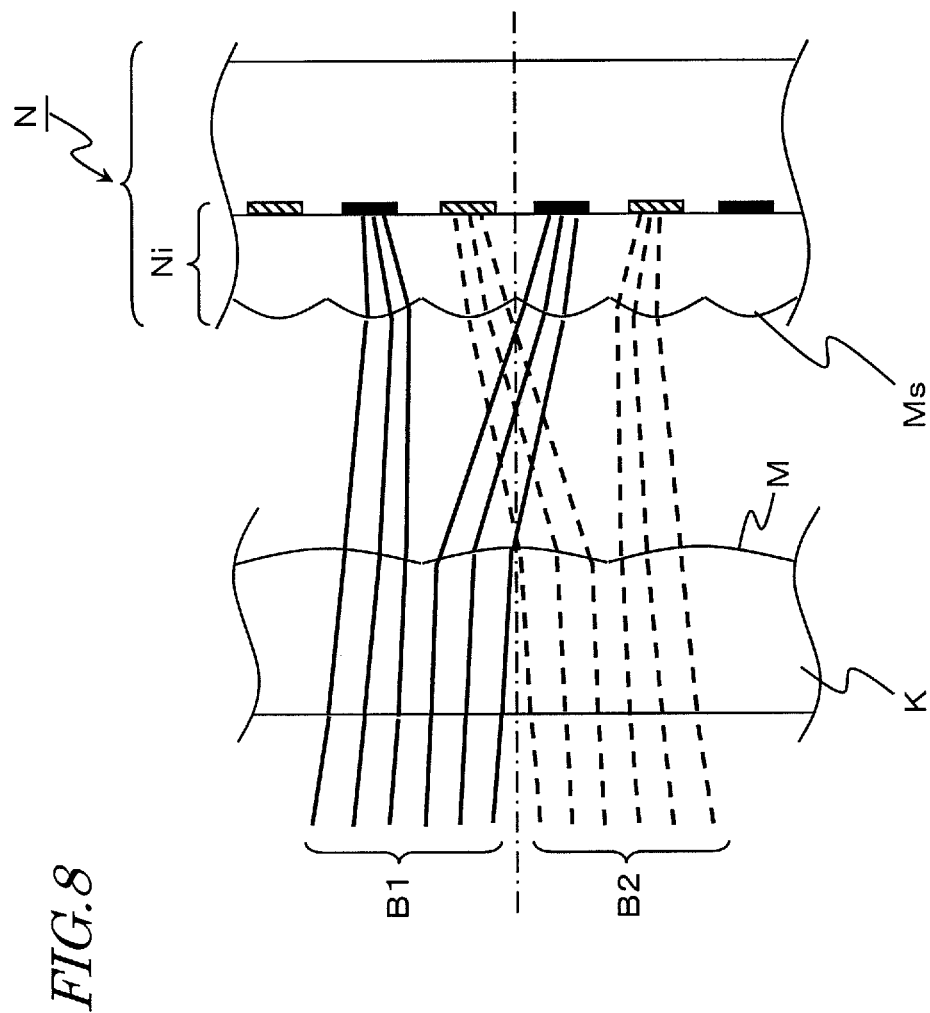
FIG. 8 is an enlarged view of the array of optical elements and image sensor according to the second embodiment.

FIG. 8 is an enlarged view of the array of optical elements K and image sensor N shown in FIG. 5. The image sensor N includes a plurality of pixels which are arranged two-dimensionally in columns and rows. Each of those pixels is defined by a photoelectrically converting section. The array of optical elements K is arranged so that the lenticular lens surface with the optical elements M faces the image sensor N. As shown in FIG. 5, the array of optical elements K is arranged in the vicinity of the focal point of the lens optical system L at a predetermined distance from the image sensor N. On the image capturing plane Ni, micro lenses Ms are arranged so as to cover the respective surfaces of the pixels. The arrangement of the array of optical elements K is determined with respect to the focal point of the objective lens L1. The array of optical elements K is configured so that one period of the cylindrical faces of the array of optical elements K corresponds to two of the pixels on the image capturing plane Ni.

The array of optical elements K is arranged so that each optical element M is associated with two rows of pixels on the image capturing plane Ni and has the function of changing the light-outgoing directions according to the angle of incidence of the incoming light beam. Specifically, most of the light beam B1 transmitted through the optical region D1 is incident on an odd-numbered row of pixels, which form a first group of pixels, on the image capturing plane Ni, and most of the light beam B2 transmitted through the optical region D2 is incident on an even-numbered row of pixels, which form a second group of pixels, on the image capturing plane Ni. This can be done by appropriately designing the refractive index of the lenticular lens used as the array of optical elements K, the radius of curvature of the optical elements M, the distance from the image capturing plane Ni and other parameters.

Each pixel of the image sensor N photoelectrically converts the incident light and outputs an image signal Q0 to a signal processing section C. In response, the signal processing section C generates, based on the image signal Q0, an image A in which data on an odd-numbered column has been extracted as a first group of pixels and an image B in which data on an even-numbered column has been extracted as a second group of pixels.

The image A obtained through this processing has been generated based on the light beam that has been transmitted through the optical region D1. On the other hand, the image B has been generated based on the light beam that has been transmitted through the optical region D2. That is to say, these images A and B are an image produced by a polarized light component that is parallel to the polarization direction of the polarized light source 51 and an image produced by a polarized light component that is perpendicular to the polarization direction of the polarized light source, respectively. Then, signals representing the images A and B thus generated are output to the image synthesizing section 7 and subjected to the same processing there as what has already been described for the first embodiment. As a result, the same effects as those of the first embodiment can also be achieved.

In the embodiment described above, the signal processing section C and image synthesizing section 7 of the camera are supposed to be provided separately. However, the signal processing may also be carried out so that the image signal Q0 is output directly to the image synthesizing section 7 and that the image synthesizing section 7 generates signals representing the images A and B based on the image signal Q0.

Also, although the objective lens L1 is supposed to be a single lens in the embodiment described above, the objective lens L1 may also be a set of multiple lenses. If a set of lenses is used, the optical design can be made with an increased degree of freedom, and therefore, an image with a high resolution can be obtained, which is beneficial.

To allow the array of optical elements K to split light beams as intended, the image capturing lens optical system may have image-space telecentricity. However, even if the image capturing lens does not have image-space telecentricity, the effect of splitting the light beams can also be achieved just as intended by appropriately adjusting the period of the array of optical elements (such as the lenticular lens or a micro lens array) which is arranged in front of the image sensor according to the angle of emittance of an off-axis principal beam of the image capturing optical system. In that case, the overall size of the image capturing lens optical system can be reduced.

Embodiment 3

Hereinafter, a third embodiment of an imaging-observation apparatus will be described. The imaging-observation apparatus of this embodiment includes an image capturing section 41", which is a major difference from the first and second embodiments. Thus, the following description of this embodiment will be focused on the structure of the image capturing section 41".

Figure 9:
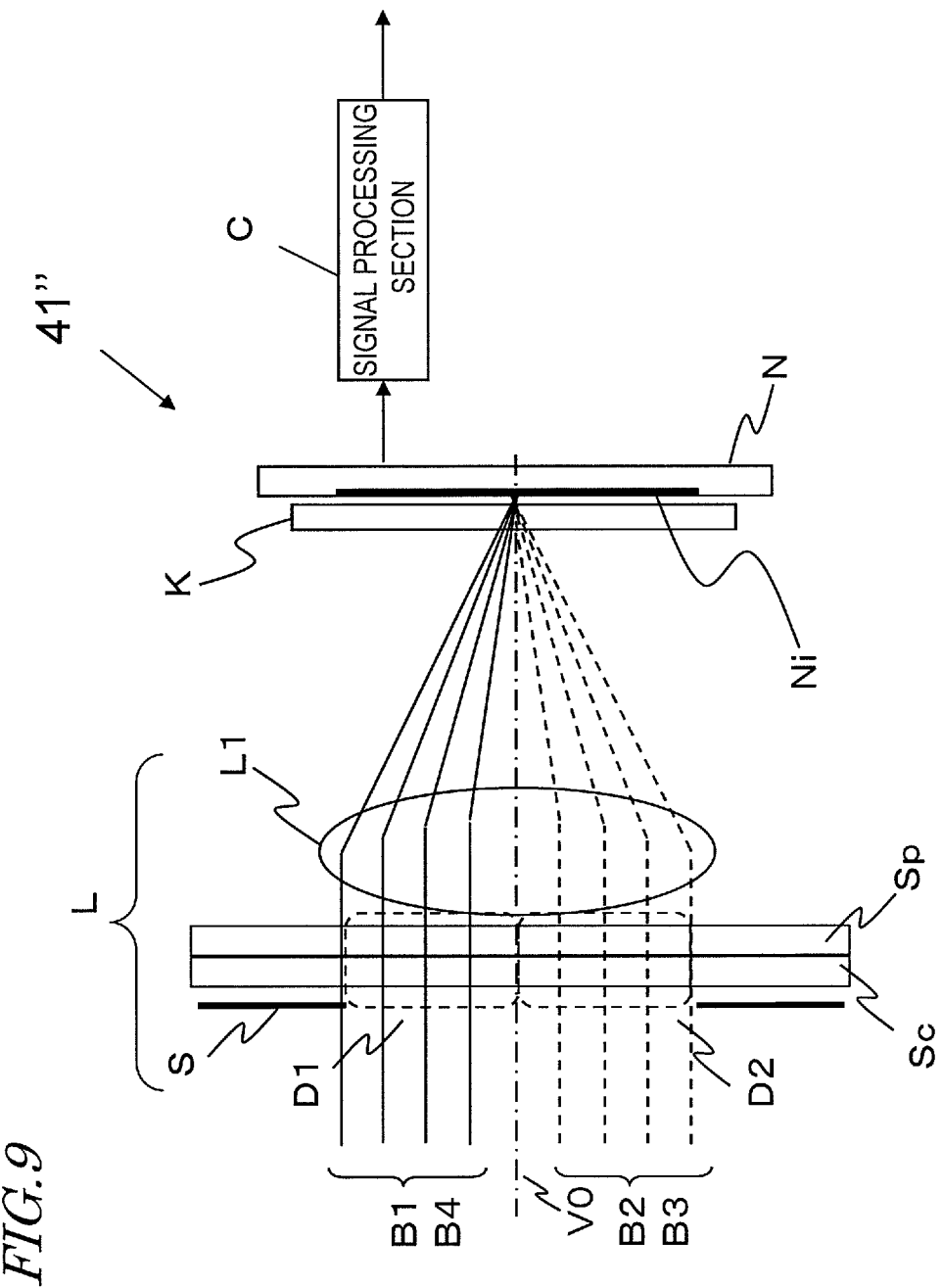
FIG. 9 illustrates a configuration for an image capturing section according to a third embodiment.

FIG. 9 schematically illustrates the structure of the image capturing section 41" of the imaging-observation apparatus according to this embodiment. The image capturing section 41" includes a lens optical system L of which the optical axis is identified by V0, an array of optical elements K which is arranged in the vicinity of the focal point of the lens optical system L, and an image sensor N. The lens optical system L includes a stop S, an objective lens L1 which images the light that has been transmitted through the stop S onto the image sensor N, and an area-divided polarizer Sp and an area-divided color filter Sc which are arranged in the vicinity of the stop S. In this embodiment, the polarization direction and wavelength of the light to generate an image are used as shooting optical conditions.

In this embodiment, the lens optical system L has four optical regions and a micro lens array is used as the array of optical elements K, which are differences from the second embodiment. Thus, the following description of this third embodiment will be focused on these structures.

Figure 10:
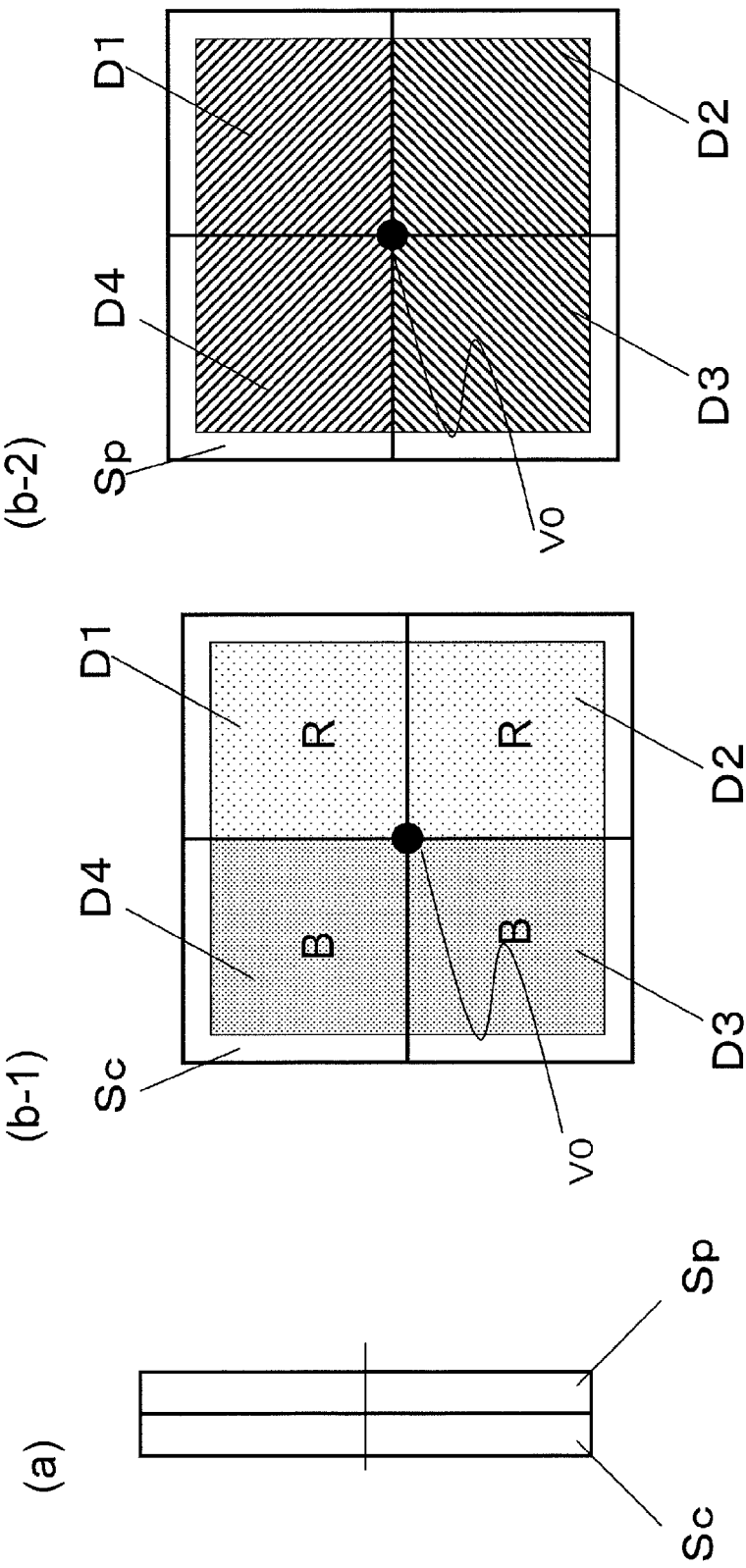
FIG. 10($a$) is a cross-sectional view of an area-divided color filter and an area-divided polarizer according to the third embodiment, FIG. 10($b$-1) is a plan view of the area-divided color filter, and FIG. 10($b$-2) is a plan view of the area-divided polarizer.

FIG. 10(*a*) is a side view of an area-divided color filter Sc and area-divided polarizer Sp which are arranged in the vicinity of the stop S of the lens optical system L according to this embodiment and FIGS. 10(*b*-1) and 10(*b*-2) are front views thereof. The area-divided color filter Sc and area-divided polarizer Sp are arranged in close contact with each other so that the area-divided color filter Sc is located closer to the subject. Specifically, FIG. 10(*b*-1) is a front view of the area-divided color filter Sc and FIG. 10(*b*-2) is a front view of the area-divided polarization filter Sp.

On a plane that intersects with the optical axis V0 of the lens optical system L at right angles, four optical regions D1 through D4 are arranged in four areas that are defined by two lines that pass through the point of intersection of the optical axis V0 and that intersect with each other at right angles. On these optical regions D1 through D4, incident respectively are the bundles of rays B1 through B4 that have come from the subject 11. As shown in FIG. 10(*b*-1), the area-divided color filter Sc has a color filter which transmits a light beam falling within the color red wavelength range (R) in the optical regions D1 and D2, and has a color filter which transmits a light beam falling within the color blue wavelength range (B) in the optical regions D3 and D4. On the other hand, the area-divided polarizer 62 has a polarizer which transmits a polarization component that is parallel to the polarization direction of the polarized light source 51 in the optical regions D1 and D4, and also has a polarizer which transmits a polarization component that is perpendicular to the polarization direction of the polarized light source 51 in the optical regions D2 and D3.

Figure 11:
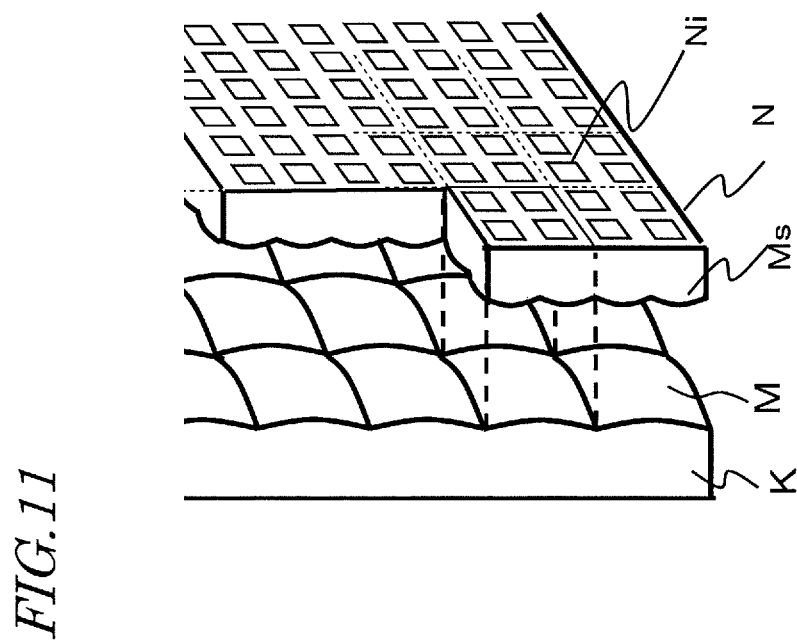
FIG. 11 is a partially cutaway perspective view of an array of optical elements and an image sensor according to the third embodiment.

FIG. 11 is a partially cutaway perspective view of the array of optical elements K and image sensor N. The array of optical elements K has an array of micro lenses, in which spherical optical faces M are arranged periodically, on its light-outgoing side. The image sensor N is arranged so as to face the array of optical elements K. Each of the pixels on the image capturing plane Ni of the image sensor N is provided with a micro lens Ms. One period of the array of micro lenses M of the array of optical elements K is set to be twice as long as Ms both horizontally and vertically. That is why a single lens element M of the array of micro lenses that form the array of optical elements K is associated with four pixels on the image capturing plane Ni.

Figure 12:
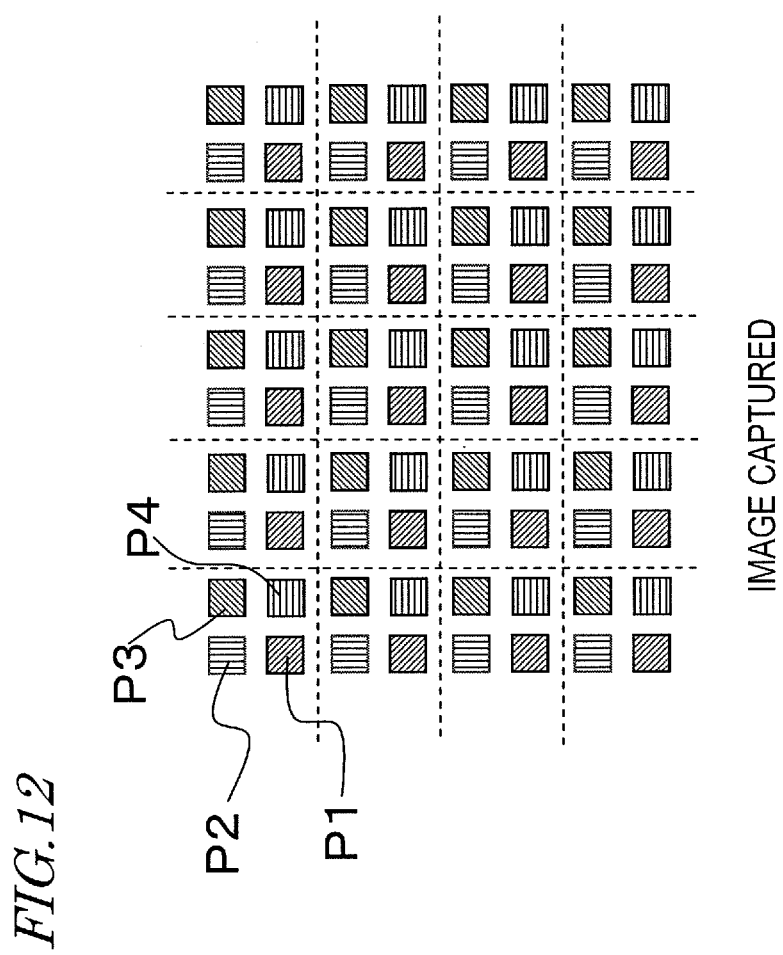
FIG. 12 illustrates how light beams are incident on respective pixels of an image sensor according to the third embodiment.

FIG. 12 illustrates how light beams are incident on the image sensor. A bundle of rays which has been transmitted through the optical region D1 is incident on one P1 of four pixels of the image sensor that are associated with one of lens elements M that form the array of optical elements K due to the interaction of the lens optical system L and the array of optical elements K. In the same way, the bundles of rays which have been transmitted through the optical regions D2 through D4 are incident on mutually different pixels P2, P3 and P4, respectively. As a result, on the image sensor, the light beams that have been transmitted through the optical regions D1 through D4 are imaged at pixels P1 through P4 every other pixel both horizontally and vertically using a set of four pixels (i.e., two vertical pixels by two horizontal pixels) as a set. That is to say, the light beams B1 through B4 are transmitted through the optical regions D1 through D4 and then are imaged by the array of optical elements K onto a group of pixels P1, P2, P3 and P4.

The image sensor N photoelectrically converts this incident light on a pixel-by-pixel basis and transmits an image signal Q0 thus obtained to the signal processing section C. In response, the signal processing section C reconstructs the image by decimating some pixels in accordance with the relation shown in FIG. 12, thereby generating signals representing images Q1 through Q4 produced by the light beams that have been transmitted through the optical regions D1 through D4. Specifically, the image Q1 is produced by a component of light that falls within the color red wavelength range and that is parallel to the polarization direction of the polarized light source 51. The image Q2 is produced by a component of light that falls within the color red wavelength range and that is perpendicular to the polarization direction of the polarized light source 51. The image Q3 is produced by a component of light that falls within the color blue wavelength range and that is perpendicular to the polarization direction of the polarized light source 51. And the image Q4 is produced by a component of light that falls within the color blue wavelength range and that is parallel to the polarization direction of the polarized light source 51. In this manner, according to this embodiment, four images with mutually different transmission polarization directions and wavelength ranges can be obtained per shooting session.

Figure 13:
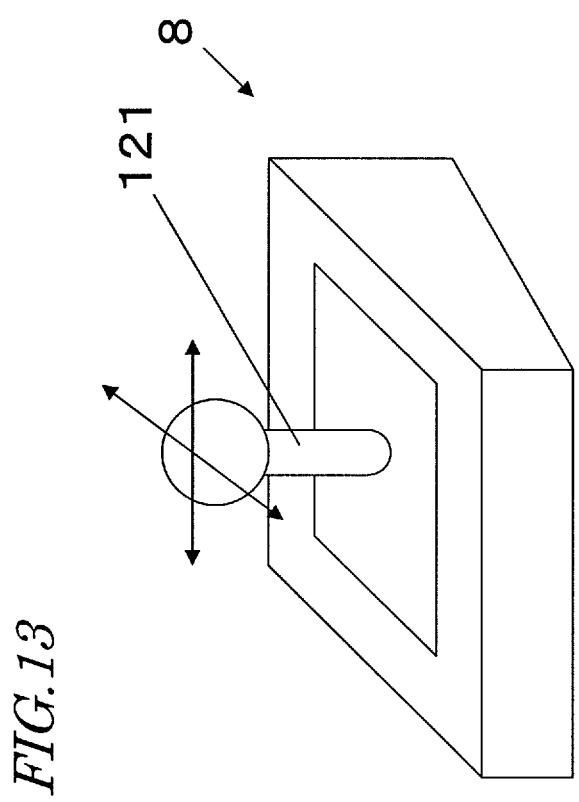
FIG. 13 is a perspective view generally illustrating a display control section according to the third embodiment.

FIG. 13 illustrates a display control section 8 according to this embodiment. This display control section 8 includes a bar control lever (joystick) 121, which can be tilted to the left and right (i.e., in the X direction) and back and forth (i.e., in the Y direction) and which outputs XY coordinates (x, y) within the range of 0 to 1 according to the magnitude of the tilt. In this case, if the lever is controlled in the X direction, the polarized light is adjusted. Specifically, when x=0, the polarized light is perpendicular to the polarization direction. On the other hand, when x=1, the polarized light is parallel to the polarization direction. Meanwhile, if the lever is controlled in the Y direction, the wavelength is adjusted. Specifically, when y=0, the polarized light falls within the color blue wavelength range. On the other hand, when y=1, the polarized light falls within the color red wavelength range. Consequently, among various (x, y) coordinates of the control lever, (1, 1), (0, 1), (0, 0) and (1, 0) are associated with the images Q1, Q2, Q3 and Q4, respectively.

Figure 14:
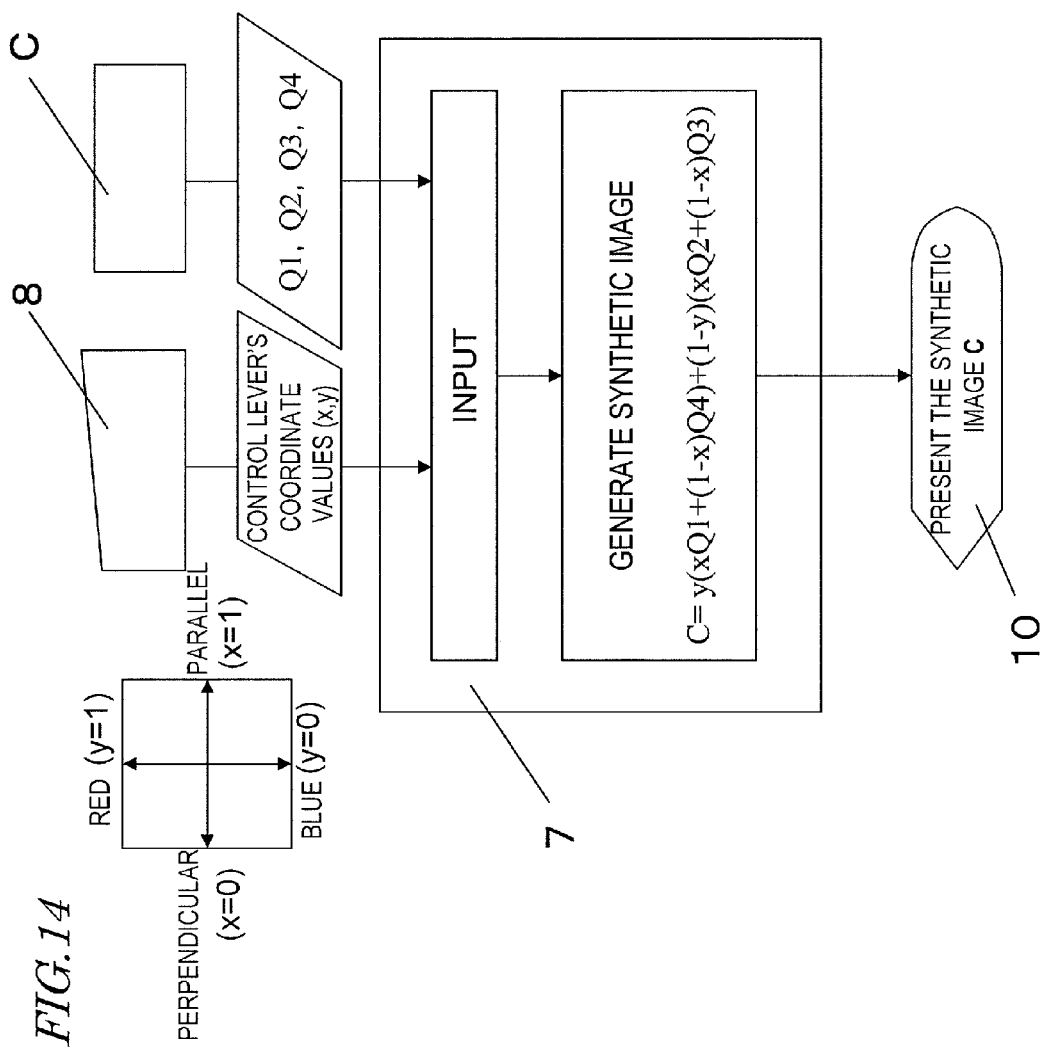
FIG. 14 illustrates generally how an image synthesizing section performs image synthesis processing according to the third embodiment.

FIG. 14 illustrates generally how the image synthesizing section 7 performs its processing according to this embodiment.

The image synthesizing section 7 receives the signals representing the images Q1 through Q4 from the signal processing section C of the image capturing section 41" of this embodiment and the output signal (x, y) of the control lever 121. In response, the image synthesizing section 7 synthesizes together the images Q1 through Q4 by the following Equation (2), sequentially generates the synthetic images C, and outputs synthetic image signals to the display section 10 one after another: . . .

$$C=y[xQ1+(1-x)Q4]+(1-y)[xQ2+(1-x)Q3] \quad (2)$$

Generally speaking, the depth that a light beam that has been incident on a person's skin reaches changes with the wavelength of the light beam. That is why if the wavelength of observation is changed, then the depth of observation also changes. Specifically, a red beam will penetrate deeper into the skin than a blue beam will. On the other hand, a skin spot can be shot more sensibly with a blue beam. That is why an image produced by a polarized light beam which falls within the color red wavelength range and which is polarized perpendicularly to the polarization direction of the polarized light source represents a person's skin which is less affected by internal spots or skin surface texture. On the other hand, an image produced by a polarized light beam which falls within the color blue wavelength range and which is polarized perpendicularly to the polarization direction of the polarized light source represents a person's skin spots clearly. That is why if the operator moves the control lever 121 shown in FIG. 13 from the left side to the down side, then he or she can observe a moving picture that looks as if the spots were emerging onto the skin surface. In this manner, the observer can observe an image by arbitrary adjusting the wavelength of observation and the polarization direction with the control lever turned. As a result, a variation in the observed image of the subject due to a difference in shooting condition can be monitored with a moving picture, and spots can be observed with more visibility.

Optionally, the area-divided color filter Sc and the area-divided polarizer Sp may have any other configuration. For example, as shown in FIG. 15(b-1), the area-divided color filter Sc may have a color filter which transmits a light beam falling within the color red wavelength range (R) in the optical region D1, a color filter which transmits a light beam falling within the color green wavelength range (G) in the optical region D2, and a color filter which transmits a light beam falling within the color blue wavelength range (B) in the optical regions D3 and D4. Meanwhile, as shown in FIG. 15(b-2), the area-divided polarization filter Sp may have a polarizer which transmits a polarization component parallel to the polarization direction of the polarized light source 51 in the optical region D3, a polarizer which transmits a polarization component perpendicular to the polarization direction of the polarized light source 51 in the optical region D4, and a non-polarized glass plate, of which the optical path length is approximately as long as that of the polarizers arranged in the optical regions D3 and D4, in the optical regions D1 and D2.

In this case, a non-polarized image shot falling within the color red wavelength range is obtained as the image Q1. A non-polarized image shot falling within the color green wavelength range is obtained as the image Q2. An image shot produced by a polarized light beam that is parallel to the polarization direction of the polarized light source within the color blue wavelength range is obtained as the image Q3. And an image shot produced by a polarized light beam that is perpendicular to the polarization direction of the polarized light source within the color blue wavelength range is obtained as the image Q4. By adopting this configuration, the subject 11 can be shot with the wavelength range divided more finely. As a result, a subtle difference in the skin image captured according to the wavelength can be observed more finely. And by observing a moving picture representing a transition between those images, the difference can be sensed with more visibility.

Optionally, the image capture device of the embodiment described above may be replaced with four monochrome cameras to capture images under mutually different shooting conditions by arranging a polarizer and a color filter in each of those cameras. Or the image capture device may also be replaced with two color cameras to capture images under mutually different polarization and wavelength situations by arranging polarizers with different polarization conditions in front of those cameras. Even so, the same effects as those of the embodiment described above can also be achieved.

Alternatively, an image of the subject may also be shot using an area-divided color filter Sc with filters that transmit light beams falling within four different wavelength ranges without using any area-divided polarizer. That is to say, only the wavelength of light to produce an image may be used as a shooting optical condition. In that case, the wavelength ranges to use may be selected from not only the visible radiation range including colors blue, green and red ranges but also from other invisible radiation ranges such as ultraviolet, near-ultraviolet and near-infrared ranges. If the wavelength range for shooting is narrowed, an observed image specific to that wavelength range can be obtained. That is why by presenting a transitional moving picture between that and other wavelength ranges, the difference between those images can be sensed with good visibility.

Other Embodiments

In the image capturing section 41' of the second embodiment, the divided polarizer Sp is arranged in the vicinity of the stop S. However, the polarizer may also be arranged on the pixels of the image sensor N. For example, the polarizer may have a pixel arrangement in which pixels covered with a first type of polarizers that transmit mostly a polarized light beam parallel to the polarization direction of a polarized light source and pixels covered with a second type of polarizers that transmit mostly a polarized light beam perpendicular to the polarization direction of the polarized light source are arranged in a checkerboard pattern. In that case, as the shooting lens system L, an ordinary optical system with no divided polarizers Sp may be used. If an image generated from pixels with the first type of polarizers is used as A and if an image generated from pixels with the second type of polarizers is used as B among various signals supplied from the image sensor N, the processing can be carried out as in the second embodiment described above. In such a situation, a lens for an ordinary camera may be used as the shooting lens system, and therefore, the lens can be selected more flexibly.

Also, the display control section 8 is supposed to have the rotary dial 9 in the first embodiment and the control lever 121 in the third embodiment. However, the display control section 8 may also have any other structure. For example, a mouse, a touchscreen panel, a keyboard or any other input device may also be used as the display control section 8. Or the operator's input may also be accepted by making the camera recognize his or her gesture as an image.

Also, according to the first through third embodiments, in a situation where multiple images that have been shot under mutually different shooting optical conditions are synthesized together, if those images to synthesize have mutually different brightness levels, then the brightness of the resultant synthetic image may vary with the control of the display control section 8 and may present a moving picture which is not comfortable to view. In that case, the image synthesizing section may perform image processing by adjusting the gain so that the overall luminance values of the multiple images that have been shot under multiple different shooting optical conditions before the synthesis become constant between those images or that the overall luminance value of the synthetic image becomes constant.

The imaging-observation apparatus of the present disclosure presents a moving picture representing a transition between a number of images that have been shot under multiple different shooting conditions to the observer in accordance with his or her control. As a result, the difference between those images can be sensed more visually and the present disclosure can be used effectively to observe multiple images that have been shot with the polarization conditions changed in order to observe a person's skin, for example. And the present disclosure can be used effectively not only in such skin observation but also in monitoring images that have been shot for measuring purposes under multiple different shooting conditions in order to shoot a multi-spectrum or an industrial polarization images in some sensing-related applications.

While the present invention has been described with respect to exemplary embodiments thereof, it will be apparent to those skilled in the art that the disclosed invention may be modified in numerous ways and may assume many embodiments other than those specifically described above. Accordingly, it is intended by the appended claims to cover all modifications of the invention that fall within the true spirit and scope of the invention.

This application is based on Japanese Patent Application No. 2012-164708 filed Jul. 25, 2012, the entire contents of which are hereby incorporated by reference.

What is claimed is:

1. An imaging-observation apparatus comprising:
an image capturing section configured to shoot a subject under multiple different shooting optical conditions at the same time and sequentially generate a plurality of images under those multiple different shooting optical conditions;
a display control section configured to accept an operator's input;
an image synthesizing section configured to synthesize together the plurality of images in accordance with the input to the display control section at a synthesis ratio specified by the input and to sequentially generate synthetic images one after another;
a display section configured to present the synthetic images; and
a polarized light source that emits mostly polarized light with a predetermined polarization direction,
wherein the subject is irradiated with the polarized light,
wherein the image capturing section includes:
a stop;
an image capturing optical system;
an image sensor with multiple groups of pixels, each said group of pixels being made up of a plurality of pixels;
an area-divided optical element which is arranged in the vicinity of the stop and which has at least two optical regions, through which light beams are transmitted with mutually different optical properties; and
an array of optical elements which is arranged between the image capturing optical system and the image sensor and which makes the light beams that have been transmitted through the predetermined optical regions of the area-divided optical element incident on mutually different groups of pixels of the image sensor, and
wherein the plurality of images are generated from the multiple groups of pixels.

2. The imaging-observation apparatus of claim 1, wherein the multiple different shooting optical conditions include a condition for shooting an image of the subject by getting the polarized light transmitted through a polarizer, of which the polarization axis is parallel to the predetermined polarization direction, and/or a condition for shooting an image of the subject by getting the polarized light transmitted through a polarizer, of which the polarization axis is perpendicular to the predetermined polarization direction.

3. The imaging-observation apparatus of claim 1, wherein the multiple different shooting optical conditions include a condition for shooting the subject with light beams falling within multiple different wavelength ranges.

4. The imaging-observation apparatus of claim 3, wherein the multiple different wavelength ranges include at least one of an ultraviolet range and an infrared range.

5. The imaging-observation apparatus of claim 3, wherein the image capturing section includes a plurality of image capture devices, and
wherein at least one of the plurality of image capture devices has a different shooting wavelength range from the other image capture devices'.

6. The imaging-observation apparatus of claim 5, wherein the at least one image capture device's shooting wavelength range is one of the infrared and ultraviolet wavelength ranges, and
wherein the other image capture devices' shooting wavelength range is the other of the infrared and ultraviolet wavelength ranges.

7. The imaging-observation apparatus of claim 1, wherein the image capturing section includes a plurality of image capture devices with respectively independent optical systems.

8. The imaging-observation apparatus of claim 7, further comprising a first polarizer,
wherein the plurality of image capture devices include a first image capture device, and
wherein the first polarizer is arranged between the subject and the first image capture device.

9. The imaging-observation apparatus of claim 8, wherein the first polarizer has a polarization axis that is either parallel or perpendicular to the predetermined polarization direction.

10. The imaging-observation apparatus of claim 8, further comprising a second polarizer,
wherein the plurality of image capture devices include a second image capture device, and
wherein the second polarizer is arranged between the subject and the second image capture device, and
wherein the first and second polarizers have mutually different polarization axis directions.

11. The imaging-observation apparatus of claim 1, wherein the area-divided optical element has an optical property that makes light beams transmitted through the at least two optical regions have mutually different polarization directions.

12. The imaging-observation apparatus of claim 11, wherein the at least two optical regions of the area-divided optical element include at least one of a region which transmits a light beam that is polarized parallel to the predetermined polarization direction and a region which transmits a light beam that is polarized perpendicularly to the predetermined polarization direction.

13. The imaging-observation apparatus of claim 11, wherein the area-divided optical element further includes an optical region which transmits a light beam that is not polarized in any direction.

14. The imaging-observation apparatus of claim 1, wherein in the area-divided optical element, the at least two optical regions have mutually different spectral transmittances.

15. The imaging-observation apparatus of claim 14, wherein in the area-divided optical element, one of the at least two optical regions selectively transmits either an ultraviolet beam or an infrared beam.

16. The imaging-observation apparatus of claim 1, wherein the plurality of images are moving pictures, and
wherein the synthetic image is a synthetic moving picture, and
wherein the display section presents the synthetic moving picture.

17. An imaging-observation apparatus comprising:
an image capturing section configured to shoot a subject under multiple different shooting optical conditions at the same time and generate a plurality of images under those multiple different shooting optical conditions;
a display control section configured to accept an operator's input;
an image synthesizing section configured to synthesize together the plurality of images to generate a synthetic image, the image synthesizing section generating a first synthetic image by synthesizing together the plurality of images in accordance with a first input that has been entered through the display control section at a synthesis ratio specified by the first input, and generating a second synthetic image by synthesizing together the plurality of images in accordance with a second input that has been entered after the first input through the display control section at a synthesis ratio specified by the second input;
a display section configured to present the first synthetic image and then the second synthetic image; and
a polarized light source that emits mostly polarized light with a predetermined polarization direction,
wherein the subject is irradiated with the polarized light,
wherein the image capturing section includes:
a stop;
an image capturing optical system;
an image sensor with multiple groups of pixels, each said group of pixels being made up of a plurality of pixels;
an area-divided optical element which is arranged in the vicinity of the stop and which has at least two optical regions, through which light beams are transmitted with mutually different optical properties; and
an array of optical elements which is arranged between the image capturing optical system and the image sensor and which makes the light beams that have been transmitted through the predetermined optical regions of the area-divided optical element incident on mutually different groups of pixels of the image sensor, and
wherein the plurality of images are generated from the multiple groups of pixels.

18. An imaging-observation apparatus comprising:
an image capturing section configured to shoot a subject under multiple different shooting optical conditions at the same time and generate a plurality of images under those multiple different shooting optical conditions;
a display control section configured to accept an operator's input;
an image synthesizing section configured to synthesize together the plurality of images to generate a synthetic image, the image synthesizing section generating a first synthetic image by synthesizing together a first plurality of images that have been generated by the image capturing section at a first time in accordance with a first input that has been entered through the display control section at a synthesis ratio specified by the first input, and generating a second synthetic image by synthesizing together a second plurality of images that have been generated by the image capturing section at a second time after the first time in accordance with a second input that has been entered after the first input through the display control section at a synthesis ratio specified by the second input;
a display section configured to present the first synthetic image and then the second synthetic image; and
a polarized light source that emits mostly polarized light with a predetermined polarization direction,
wherein the subject is irradiated with the polarized light,
wherein the image capturing section includes:
a stop;
an image capturing optical system;
an image sensor with multiple groups of pixels, each said group of pixels being made up of a plurality of pixels;
an area-divided optical element which is arranged in the vicinity of the stop and which has at least two optical regions, through which light beams are transmitted with mutually different optical properties; and
an array of optical elements which is arranged between the image capturing optical system and the image sensor and which makes the light beams that have been transmitted through the predetermined optical regions of the area-divided optical element incident on mutually different groups of pixels of the image sensor, and
wherein the plurality of images are generated from the multiple groups of pixels.

* * * * *